(12) United States Patent
Muggiasca et al.

(10) Patent No.: US 12,366,101 B2
(45) Date of Patent: Jul. 22, 2025

(54) MAGNETICALLY OPERATED CLOSING DEVICE FOR CONTROLLED CONTAMINATION EQUIPMENT

(71) Applicant: DE LAMA S.P.A., San Martino Siccomario (IT)

(72) Inventors: Andrea Muggiasca, Pavia (IT); Paolo Bianchi, Pavia (IT)

(73) Assignee: DE LAMA S.P.A., San Martino Siccomario (IT)

( * ) Notice: Subject to any disclaimer, the term of this patent is extended or adjusted under 35 U.S.C. 154(b) by 882 days.

(21) Appl. No.: 17/621,733

(22) PCT Filed: Jun. 24, 2020

(86) PCT No.: PCT/IB2020/055971
§ 371 (c)(1),
(2) Date: Dec. 22, 2021

(87) PCT Pub. No.: WO2020/261142
PCT Pub. Date: Dec. 30, 2020

(65) Prior Publication Data
US 2022/0251894 A1    Aug. 11, 2022

(30) Foreign Application Priority Data

Jun. 24, 2019  (IT) .................. 102019000009960

(51) Int. Cl.
*E05F 15/643*  (2015.01)
*A61L 2/07*  (2006.01)
(Continued)

(52) U.S. Cl.
CPC .............. *E05F 15/643* (2015.01); *A61L 2/07* (2013.01); *A61L 2/206* (2013.01); *A61L 2/208* (2013.01);
(Continued)

(58) Field of Classification Search
CPC .......... E05F 15/643; A61L 2/07; A61L 2/206; A61L 2/208
See application file for complete search history.

(56) References Cited

U.S. PATENT DOCUMENTS 6,416,144 B1    7/2002 Houston et al.
2003/0111470 A1    6/2003 Fouillet et al.

FOREIGN PATENT DOCUMENTS

DE    20 2006 016293 U1    3/2007
EP    1 310 353 A1    5/2003
WO    01/74409 A1    10/2001

OTHER PUBLICATIONS

International Search Report, PCT/IB2020/055971, 3 pages.
(Continued)

*Primary Examiner* — Sean E Conley
(74) *Attorney, Agent, or Firm* — Francis J. Maguire; WARE FRESSOLA MAGUIRE & BARBER LLP

(57) ABSTRACT

A linear stem (3) guides a sliding door (11), which is dragged by a magnetic drive unit between an operating position (W), in which it covers and closes an access mouth (20) to an internal compartment (21) of a sterilizer (1), and an inoperative or opening (N), in which the door (11) moves to a position next to the access mouth (20), thus making it accessible from the outside.
The sliding door (11) is operated by movement members (5), comprising a linear module (50), adapted to house a transmission belt (52) stretched between two return wheels (53), one of which is driven by an electric gearmotor (54); a branch of the transmission belt (52) carries a slider (55) with a permanent magnet (56), facing a magnetic plate (6) fixed to the sliding door (11) which is dragged by the magnetic field generated by the cursor (55) in motion.

11 Claims, 5 Drawing Sheets

(51) Int. Cl.
*A61L 2/20* (2006.01)
*E05F 15/665* (2015.01)
(52) U.S. Cl.
CPC ... *A61L 2202/121* (2013.01); *A61L 2202/122* (2013.01); *A61L 2202/14* (2013.01); *A61L 2202/17* (2013.01); *A61L 2202/21* (2013.01); *E05F 15/665* (2015.01); *E05Y 2201/434* (2013.01); *E05Y 2201/46* (2013.01); *E05Y 2201/64* (2013.01); *E05Y 2201/652* (2013.01); *E05Y 2201/668* (2013.01); *E05Y 2201/684* (2013.01); *E05Y 2800/12* (2013.01); *E05Y 2800/28* (2013.01); *E05Y 2999/00* (2024.05)

(56) References Cited

OTHER PUBLICATIONS

Written Opinion of the International Searching Authority, PCT/IB2020/055971, 7 pages.
Biblioigraphic data including English Abstract, DE202006016293U1, 1 page.

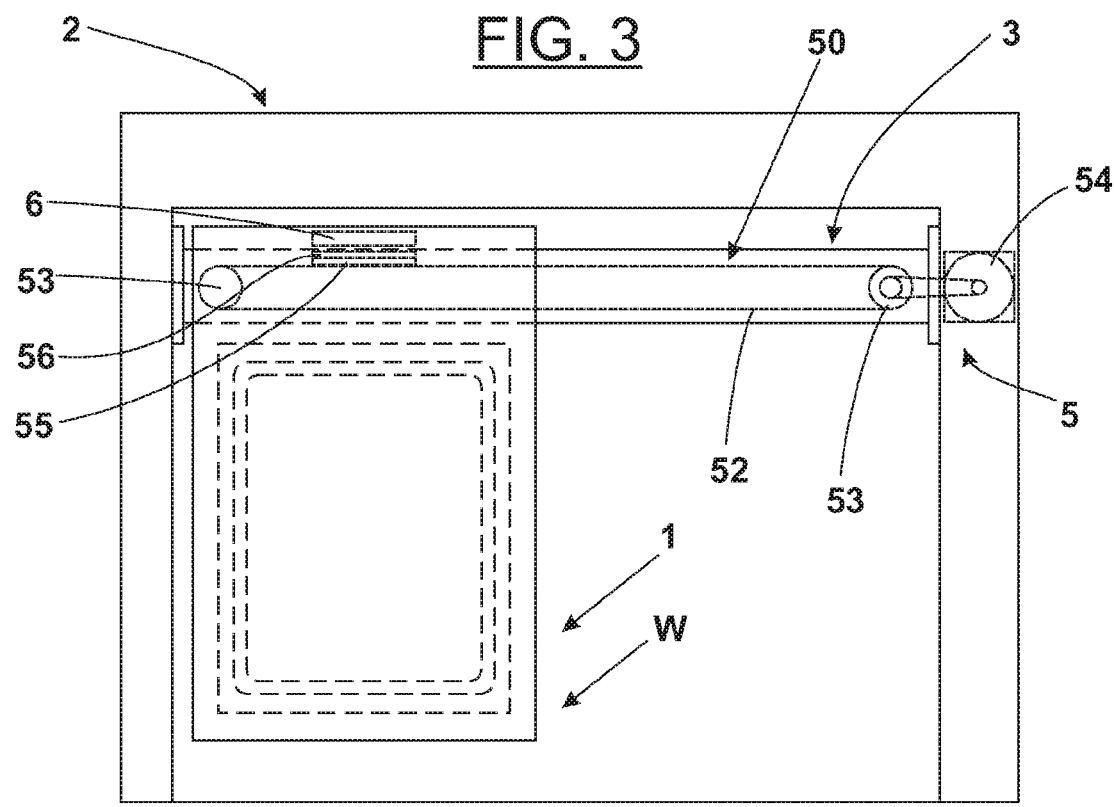
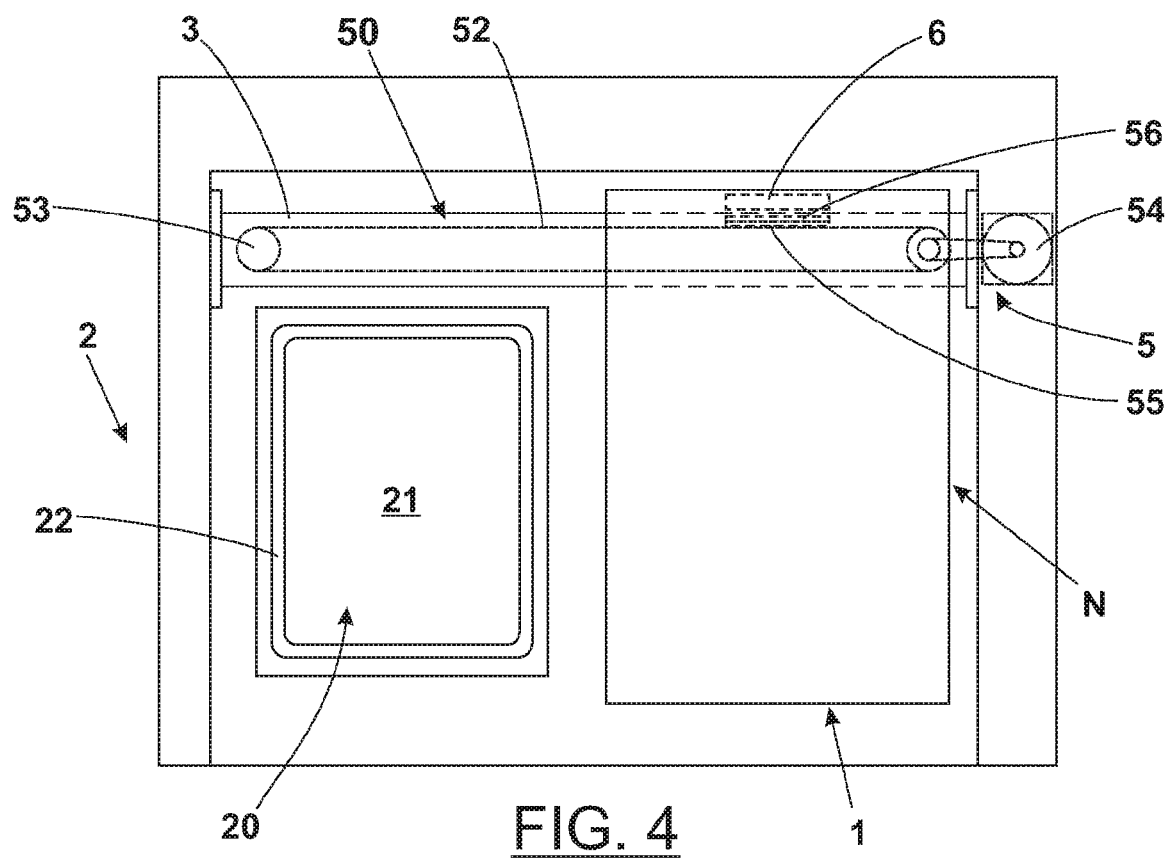

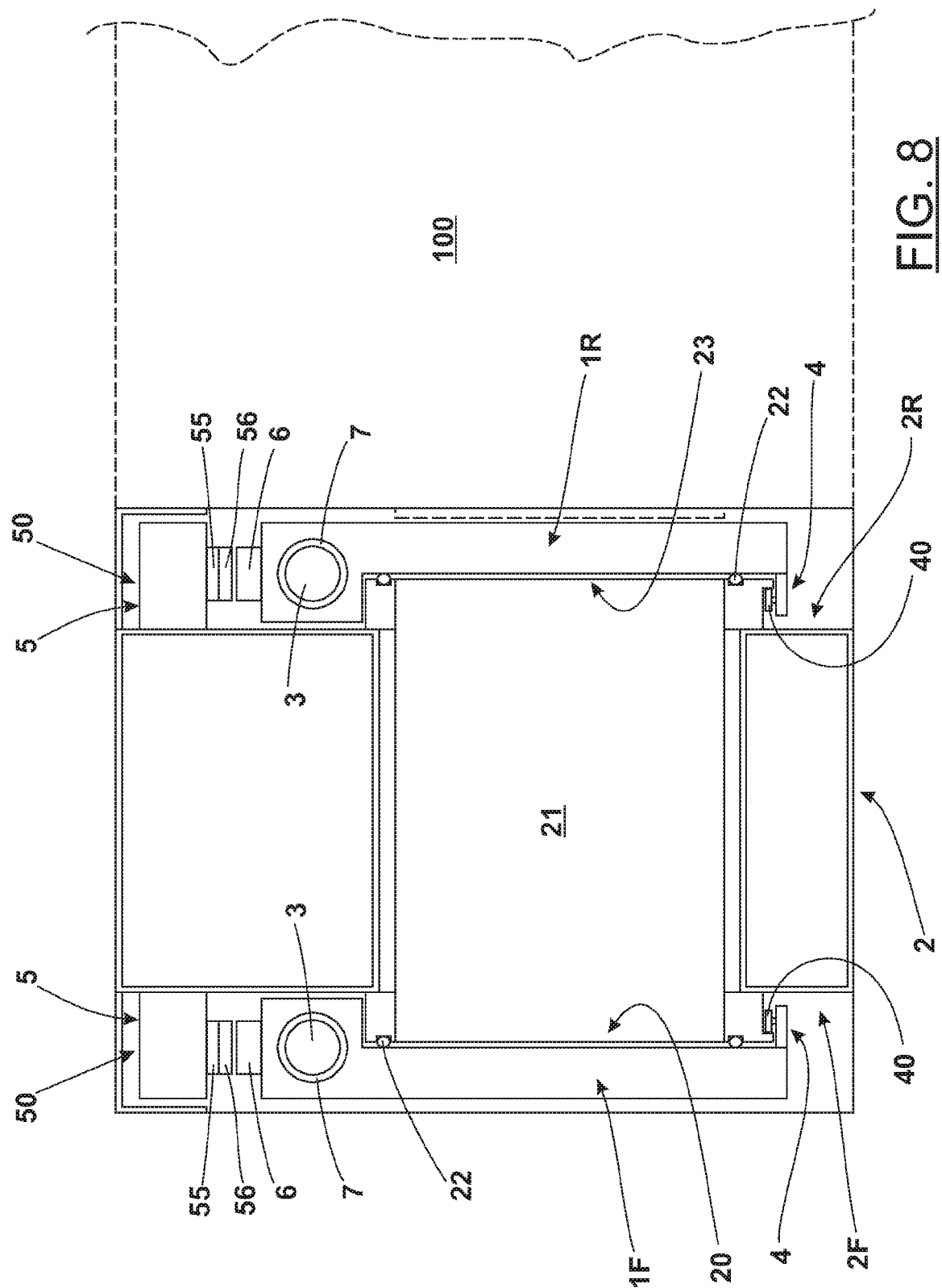

MAGNETICALLY OPERATED CLOSING DEVICE FOR CONTROLLED CONTAMINATION EQUIPMENT

TECHNICAL FIELD

The present invention refers to the special construction sector for controlled contamination equipment.

In particular, the invention relates to a magnetic-operated closing device, comprising a door and relative actuation devices, suitable for installation in low-contamination equipment, which requires sealing, and intended to operate in environments with any Class of contamination according to GGMP standards.

BACKGROUND ART

Within the scope of the invention, controlled atmosphere equipment is included, for example: insulators, which are closed rooms in which toxic products are treated or packaged or which require particular conditions of low contamination or asepsis, usually kept at a pressure less than atmospheric, and in which the operators remain outside and carry out operations using sealed gloves fixed to a wall; the clean rooms, of any Class of contamination among those provided for example in the GGMP standard (from Class A to Class D), in which the operator, after a complex and accurate disinfection and dressing operation, is made able to enter a substantially sterile environment without compromising its class of contamination; the "rabs", barriers that limit access to a limited environment, kept at a low level of contamination by a continuous flow of purified and decontaminated air; and, in general, to all controlled contamination environments, operating in any class of contamination.

The subject equipment is used in various fields, including pharmaceutical, cosmetic and food sectors, and allow to define chamber, insulated from the outside, in which various types of products are placed to be treated or packaged.

In particular, in the controlled environment packaging processes, the containers of the product to be packed are introduced into the packaging environment after being subjected to washing and sterilization operations. These latter operations are carried out in sterilizers, dryers, depyrogenation ovens, washing and disinfection machines, or in equipment that perform two or more of the above operations in combination. The sterilization operations can, for example, be carried out in an autoclave with machines that use saturated steam, a water/steam mixture, superheated water, or hydrogen peroxide or ethylene oxide (ETO).

In order to maintain the degree of sterility and low contamination obtained for the containers, the equipment described above is sealedly connected to the relative isolator, or to another controlled contamination environment.

For convenience and purely by way of example, in the description of the state of the art relating to the invention and in the detailed description of the invention itself, reference will be made to its application in a sterilizer, of the saturated steam type or equivalent, and to the connection of the latter to an isolator intended for packaging pharmaceutical products.

A saturated steam sterilizer operates at high temperatures and pressures and is designed to carry out, in consecutive cycles, the introduction of batches of containers, their treatment and their subsequent extraction and forwarding to a packaging line contained within a isolator.

To ensure correct operation, it is equipped with one or more sealed doors, designed to allow access to the containers, to isolate the sterilizer from the external environment during their sterilization operations, and finally to allow the transfer of the sterilized containers. to the packaging line contained in the insulator, without any contact with the external environment.

For this reason, a sterilizer usually has an entrance door and an exit door, the latter intended to interface the internal compartment of the sterilizer with the controlled atmosphere one of the insulator.

The sterilizer is equipped with systems for maintaining low contamination conditions, of a degree equal to that of the environment of the insulator to which it is connected, of a known type, which will not be further detailed as they are not directly relevant to the invention.

As is known to those who approach the design of such equipment, great attention must be paid to the shape of the various elements in order to limit as much as possible any accumulation areas of impurities such as, for example, dust or residues of products used in previous production operations, that are difficult to reach during cleaning and sanitizing operations.

Technical Problem

It is easy to understand how the doors represent, from this point of view, critical components, due to the presence of hinges, any members for automatic movement, lock units and more, with numerous interstices, hidden corners, the presence of lubricants, possible generation of polluting particles due to wear of parts, sliding and so on.

OBJECTS OF THE INVENTION

It is easy to understand how the doors represent, from this point of view, critical components, due to the presence of hinges, any members for automatic movement, lock units and more, with numerous interstices, hidden corners, the presence of lubricants, possible generation of polluting particles due to wear of parts, sliding and so on.

The technical problem which the present invention aims to address is therefore that of providing a magnetically operated closure device suitable for installation in a sterilizer, also in association with a subsequent isolator, as well as in other equipment operating in a controlled contamination environment, that need access with tight closures.

Another object of the invention is to propose a closing device, comprising a magnetically operated door, whose conformation has been carefully studied in all its parts to obtain surfaces that are as simple and smooth as possible, and which is free of gaps and/o points that are difficult to access in ordinary cleaning and sanitizing operations, where impurities, bacteria or other contaminants incompatible with the intended use of the door may stagnate and proliferate.

Another object of the invention is to obtain a magnetic actuation of the aforementioned door with a few simple components, which is reliable, compact, which does not generate particles due to chafing and wear, with fluid movements and also constructed in such a way as to respect the maximum the declared needs of easy cleaning and sanitization.

A further object of the invention provides that the magnetic door and the other components of the closing device are made of stainless materials, chemically stable and which allow to undergo all the cleaning treatments necessary for certification for all degrees of low contamination, required by current regulations, without their surfaces being deteriorated, damaged or releasing contaminating or harmful substances.

These and other objects are fully achieved by a magnetically operated closing device for controlled atmosphere devices, comprising a sliding door and which further comprises:
- a linear stem, supported on the outside of a frame with which the door itself is associated, in which there is an access opening to a compartment; the latter is placed in communication with a controlled atmosphere device; the stem constitutes a linear guide on which the sliding door is engaged, movable between an operating position, of closing the access mouth, and an inoperative, opening of the same access mouth;
- movement members, associated with the sliding door and designed to give the latter opening and closing strokes between the aforementioned operational and inoperative positions, and vice versa; the moving members comprise a slider, provided with a permanent magnet, movable parallel to the cylindrical stem, and a magnetic plate integral with the sliding door; the sliding door is dragged by the permanent magnet cursor for the action of the same on the magnetic plate attached to it.

BRIEF DESCRIPTION OF THE DRAWINGS

The characteristic features of the present invention will become clear from the following description of preferred embodiments of the magnetically operated door for controlled-atmosphere appliances according to the object, in accordance with what is proposed in the claims and with the aid of the attached drawings, in which:

FIGS. 3 and 4 illustrate views similar to FIGS. 1 and 2, relating to a second embodiment of the magnetically operated door;

FIG. 8 schematically illustrates, in longitudinal section, the module of FIG. 7 with the equipment with internal atmosphere only dashed.

Figure 1:
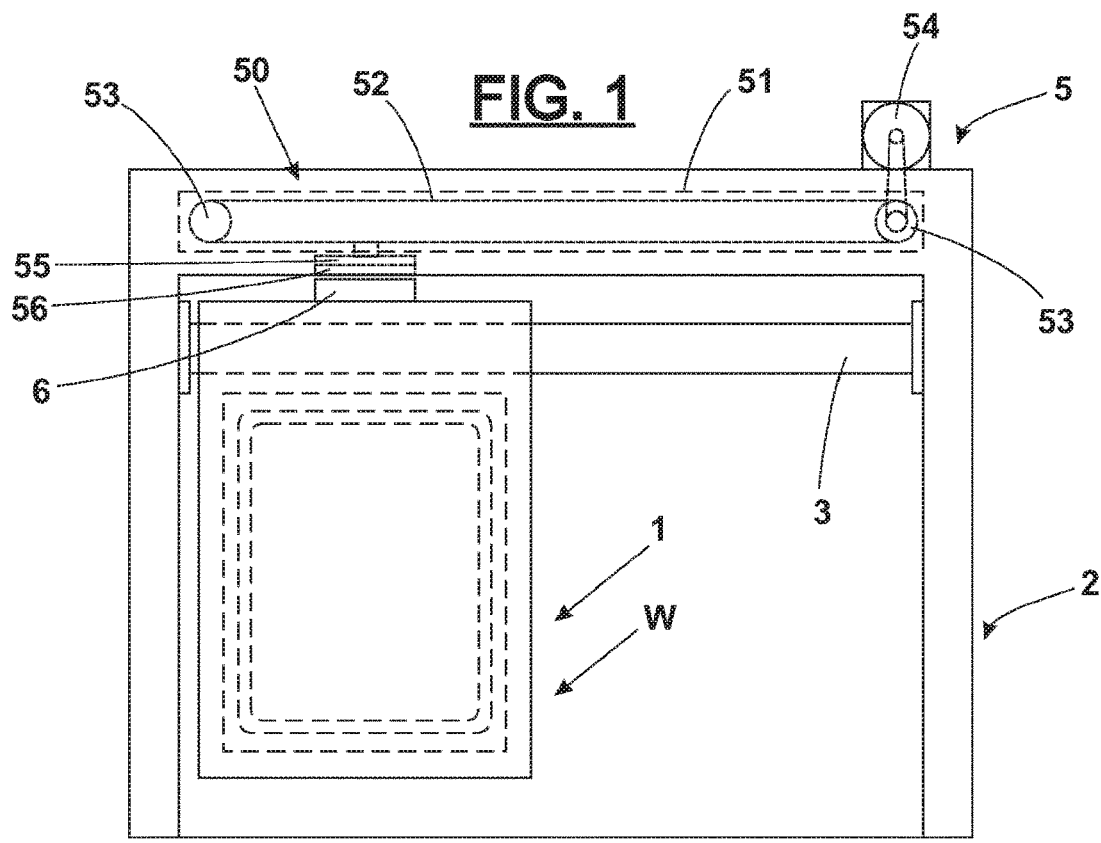
FIG. 1 shows a schematic front view of a first embodiment of the magnetically operated closing device which is the object of the invention, with the door in its closed operating position.

DESCRIPTION OF PREFERRED
EMBODIMENTS OF THE INVENTION

In the above figures, and with reference to preferred embodiments of the invention, reference number 10 has indicated a magnetic operated closing device which forms the subject of the present invention. The closing device 10, in detail, comprises a sliding door 11 and an actuation unit 12, associated with the door 11 to lead it on command, alternatively, between an inoperative or open position N and an operating or closing position W, as will be better detailed below.

The sliding door 11 is intended mainly, even if not exclusively, to be used in equipment 1 for the sterilization, washing or depyrogenation of containers intended to be filled with products to be packaged in controlled contamination environments, for example, pharmaceutical, toxic products or easily perishable. For this reason, the above devices are usually connected, by way of non-limiting example, to an isolator 100 for the packaging of pharmaceutical products.

As already mentioned in the introduction, the scope of application of the closure device 10 extends, in addition to equipment operating in the pharmaceutical sector, to similar or equivalent equipment used in the chemical, biotechnological, food or cosmetic sectors, or in any case it is in any case It is necessary to have an access opening/closing device that does not have parts that are not easily accessible, not subject to accumulation of dust or debris, and that does not have components that can themselves release dust or debris, even in small quantities.

In the illustrated embodiments of the invention, the sliding door 11 is advantageously made with a box-like shape, and has flat faces, substantially free of recesses and prominences which can limit the immediate accessibility to all its parts. The door 11 is supported by a frame 2 which constitutes the supporting structure of a saturated steam sterilizer, or of other equipment for the treatment of containers according to what has already been expressed previously. In particular, the sliding door 11 is associated with the frame 2 so as to be external and close to it.

The frame 2, made up of sheet metal panels preferably of stainless steel, conforms an access mouth 20 to a compartment 21; the latter communicates, in operational configuration, with an internal compartment of the insulator 100, and is usually crossed by means for the transport of the containers, for example a conveyor belt, not visible in the drawings for reasons of illustrative simplicity and as not directly relevant to the invention.

The frame 2 supports, on its outside, a linear rod 3, for example cylindrical, suitable for constituting a linear guide with which the sliding door 11 is engaged; the latter, as already mentioned, is movable between an operating position W, in which it is covering the aforesaid access mouth 20 to isolate the compartment 21 from the external environment, and an inoperative N, in which the sliding door 11 it is located alongside the same access mouth 20, making the compartment 21 accessible from the outside.

Figure 5:
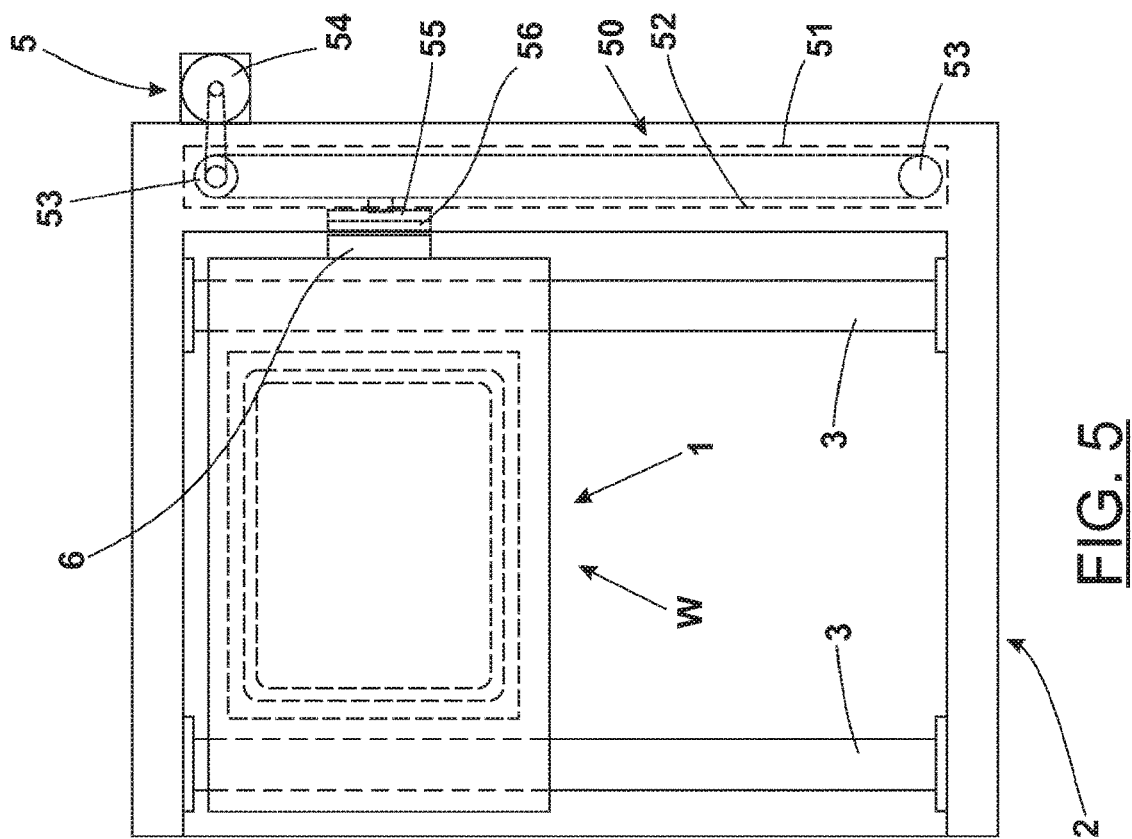

The internal face 11B of the sliding door 11, facing the access mouth 20, is provided to be pressure-pressed, in correspondence with its operating position W, by an inflatable gasket 22, arranged in a closed ring in the aforementioned frame 2, to circumscribe the access mouth 20 itself (see in particular FIG. 5).

Figure 2:
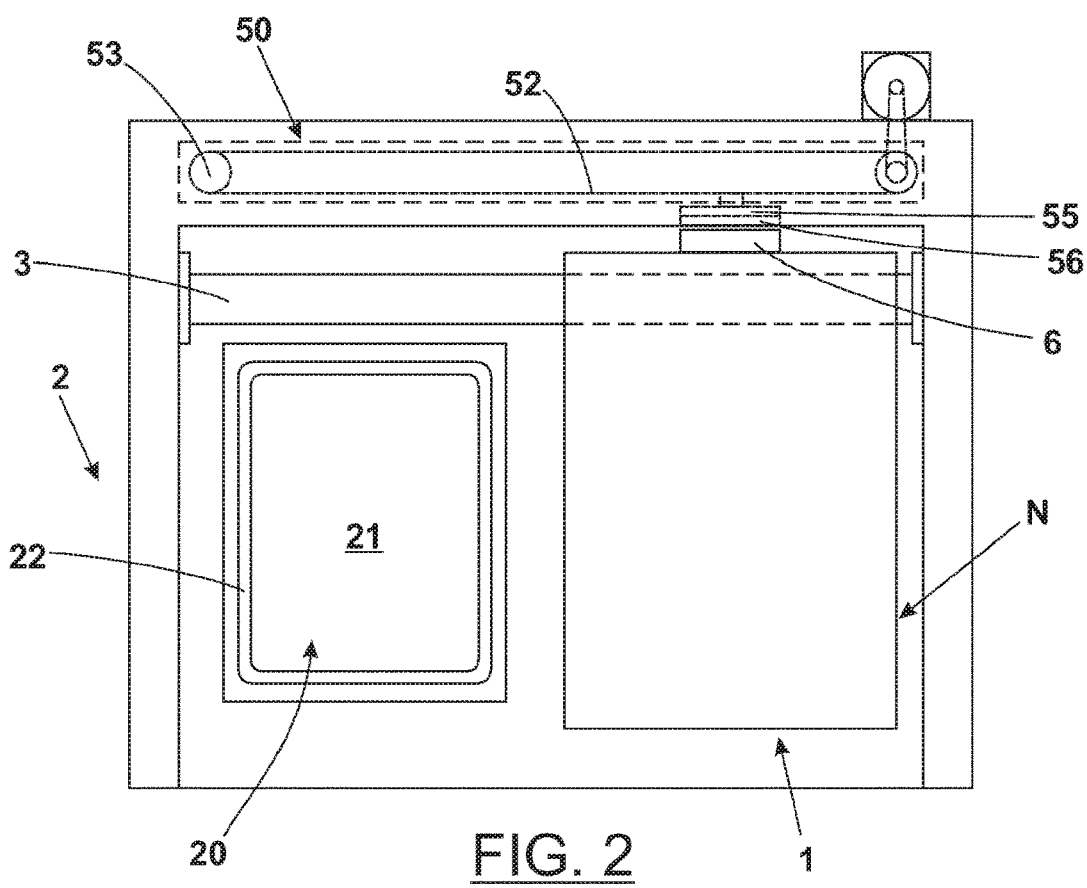
FIG. 2 illustrates a view similar to FIG. 1, with the door in the inoperative, open position.

In a first embodiment of the sliding door 11 (FIGS. 1 and 2), the latter has horizontal movement between the aforementioned operating positions W and inoperative N, with a single linear cylindrical stem 3 horizontal, which supports the sliding door 11 in the top of the latter.

Advantageously, linear guide elements 4 are also provided, suitable for keeping the lower part of the sliding door 11 close to the frame 2; the aforementioned linear guide elements 4, not described in detail as they are known, comprise sliding rollers 40 (see in particular FIG. 5), so as to have a low coefficient of friction of the rolling type between the parts in mutual movement.

The drive unit 12 is provided with moving members 5, provided to impart to the door 11 the opening and closing strokes between the aforementioned operating positions W and inoperative positions N, and vice versa.

The moving organs 5, in the first embodiment, comprise a linear module 50, arranged parallel to the top of the cylindrical stem 3 and consisting of a tubular sheath 51, inside which is housed a transmission belt 52, for example toothed, taut between two return wheels 53, one of which keyed on an electric gearmotor 54 and therefore made motive.

A branch of the transmission belt 52 has a linear cursor 55 fitted with magnets 56, suitably positioned, arranged outside the aforementioned sheath 51, intended to be dragged by the transmission belt 52.

In a preferred embodiment, the magnets 56 are permanent magnets, but according to particular needs, the adoption of electromagnets can also be provided.

The actuation unit 12 further comprises a magnetic plate 6, fixed to the upper face of the sliding door 1 so as to be counterfeited to the slider 55 and to undergo the action of the magnetic field generated by the same. The magnetic plate 6 also includes one or more permanent magnets, suitably positioned to respond to changes in the magnetic field produced by the cursor 55 with the generation of a linear thrust with direction parallel to the aforementioned cylindrical rod 3, according to the known principles that define the operation of the linear actuators and according to their construction techniques, to which reference is made for convenience.

According to the embodiments shown in the figures, a sufficient space is provided between the magnets 56 and the magnetic plate 6 to prevent contact between the two and such as to ensure the correct entrainment of the sliding door 1 by magnetic attraction.

In a second embodiment of the closing device 10 (FIGS. 3 and 4), the linear module 50 of the movement members 5 is arranged inside the aforementioned cylindrical stem 3, suitably hollow and acting as a sheath, to house the above mentioned transmission belt 52 stretched between the return wheels 53.

The aforementioned electric gearmotor 54 which drives the driving wheel 53 is located, for example, outside one of the heads of the cylindrical rod 3, while the slider 55 with the permanent magnet 56 is also arranged inside the latter and facing the overlying magnetic plate 6 associated with the sliding door 11.

In a third embodiment of the closing device 10 (FIGS. 5 and 6) the sliding movement of the door 11 is vertical; in this case two of said cylindrical rods 3 are advantageously provided, having vertical orientation and symmetrically arranged with respect to the access mouth 20.

Figure 6:
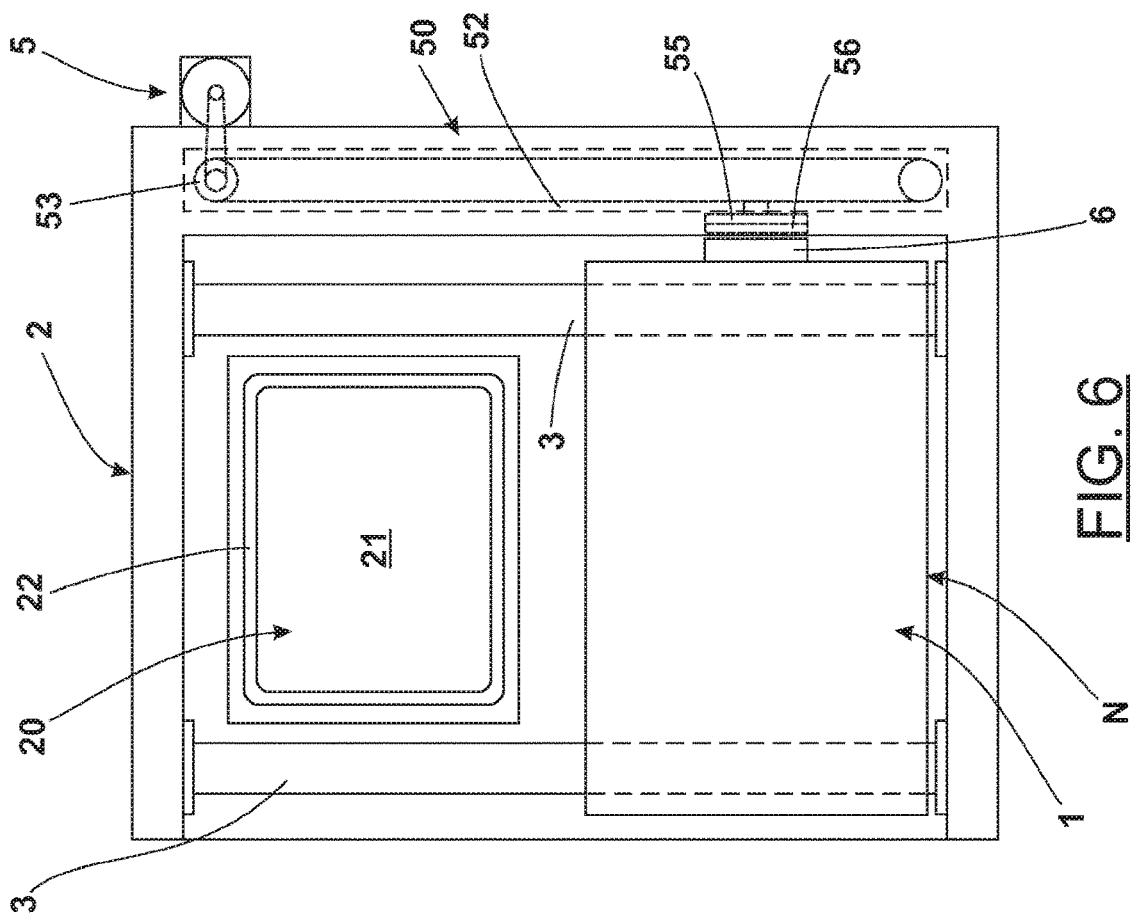
FIGS. 5 and 6 illustrate views similar to FIGS. 1 and 2, relating to a third embodiment of the magnetically operated door.

The latter is arranged at the top in the figures attached by way of example only, therefore the operating position W of the sliding door 11 is that raised in FIG. 5, while the inoperative position N, lowered, is in FIG. 6.

The moving members 5, substantially identical to what has already been said with reference to the first embodiment, are located laterally with respect to one of the cylindrical stems 5; in FIGS. 5 and 6 the moving elements 5 comprise a single linear module 50, with the associated cursor 55; however, it is possible to provide, in a variant not shown, two linear modules 50, substantially symmetrical, acting in sync on the two sides of the vertical sliding door 11.

Figure 7:
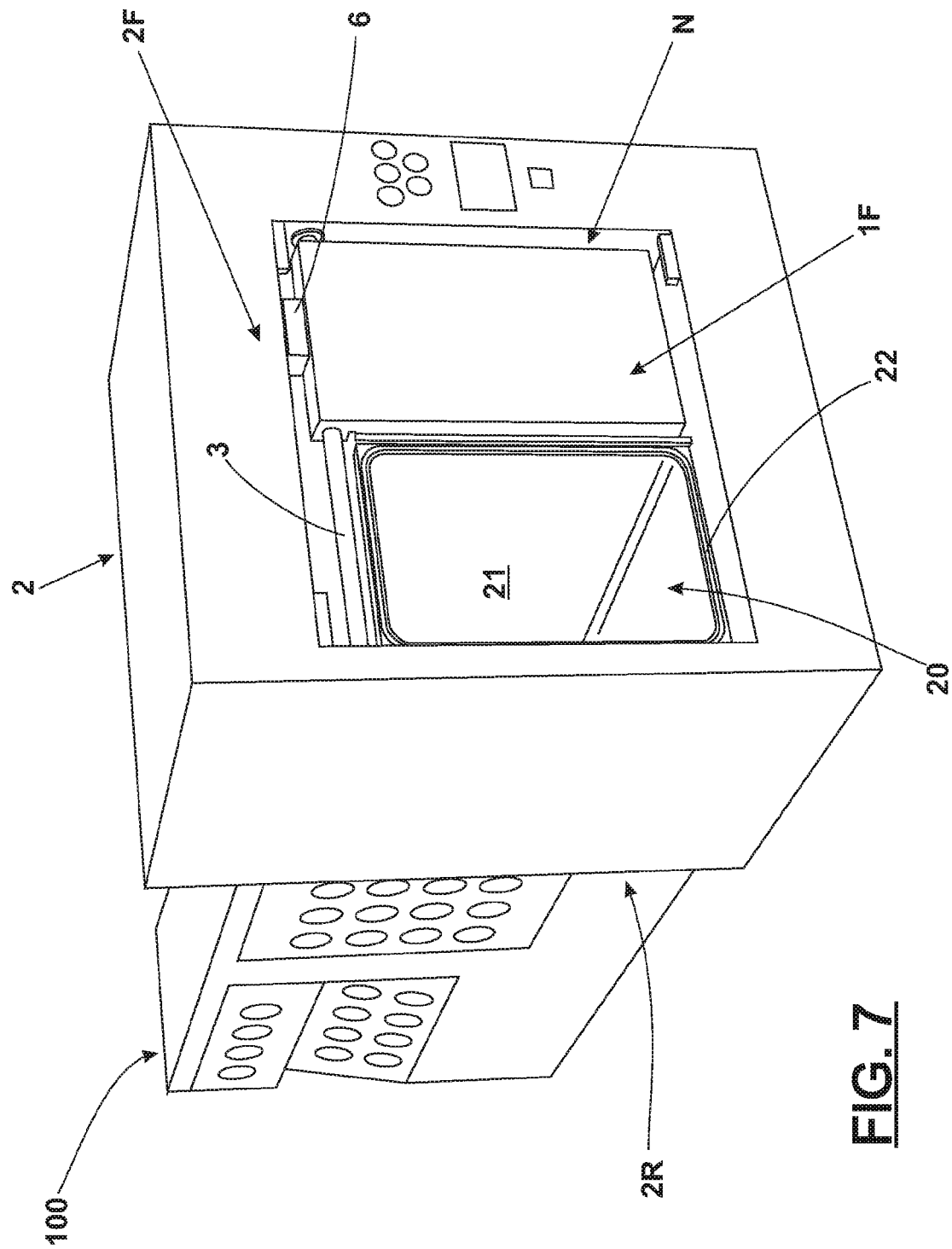
FIG. 7 shows a perspective view of a module having a front and rear magnetically operated door, combined with a controlled internal atmosphere appliance.

In FIGS. 7 and 8 are schematic perspective and side views respectively of the sterilizer 1 coupled to an insulator 100, in an operative configuration. in short, the sterilizer 1 has an external parallelepiped-shaped configuration, with a front wall 2F to which a first sliding door 11F is fixed and with a rear wall 2R with which a second sliding door 11R is associated, both sliding doors made according to the invention.

The first sliding door 1F is associated with the access mouth 20 in the front wall 2F, which flows into the compartment 21, made inside the frame 2 and capable of constituting, in this case, the operating environment for the treatment of the containers.

The second sliding door 11R is associated with an outlet 23 present in the rear wall 2R; in this way the compartment 21 of the sterilizer 1 is directly communicating with the chamber of the insulator 100 or isolated from it according to the position, respectively inoperative N or operative W of the same second sliding door 11R.

In all the embodiments of the closure device 10 described above, coupling elements 7 are provided, shown schematically in FIG. 8 and interposed between the sliding door 11 and the cylindrical stem 3. These coupling elements 7 comprise, in a substantially known manner, low friction coefficient bearings suitable for carrying out a fluid translation of the same door 1; annular sealing elements are also provided, designed to seal the door/stem coupling to prevent the entry of impurities.

To ensure perfect positional control of the door 11, the closing device 1 provides suitable position sensors, not shown, suitable for detecting and signaling the achievement of the operational closing positions W and inoperative opening positions N of the door 11 itself.

From the above description, the advantages offered by the closing device 10 object of the present invention compared with the traditional closing devices, which constitutes a valid solution for the main application of intended use, in combination with a steam sterilizer saturated, or with other similar equipment or in any case intended to treat objects in an environment with very low contamination and perfectly isolated from the outside.

Particularly advantageous is the possibility offered by the closure device 10 to conform all the components of the device so as to obtain linear and smooth surfaces, substantially free of interstices and/or points which are difficult to access in ordinary and extraordinary cleaning and decontamination operations; in this way the accumulation of substances at least potentially capable of compromising the degree of cleanliness required for the sterilizer 1, or for the other equipment with which the closing device 10 is associated is avoided.

The door 11 thus made also exhibits fluid movements and with low friction.

It is however understood that what described above has an exemplifying and non-limiting purpose, therefore any detail variations that may become necessary for technical and/or functional reasons, are considered from now on to fall within the same protective sphere defined by the claims below.

The invention claimed is:

1. A closing device for a controlled contamination device provided with environments that can be isolated from the outside, said contamination device having an internal compartment accessible by at least one access port, said closing device comprising a sliding door made with linear surfaces in a box shape and a drive unit, said closing device further comprising:

at least one cylindrical rod supported on the outside of a frame of said controlled contamination device, said cylindrical rod constituting a linear guide on which said sliding door is engaged so that the sliding door is movable between an operative position, in which the sliding door is covering an access mouth, sealing said compartment, and an inoperative position, in which the sliding door is uncovering the access mouth, unsealing said compartment;

wherein the drive unit comprises magnetic movement members associated with said frame and in turn comprising a slider a slider made with at least one magnet movable, parallel to said at least one cylindrical rod with reciprocating motion; said drive unit further comprising a magnetic plate made integral with said sliding door for being dragged by said slider due to a magnetic field generated during movements of said slider.

2. The closing device according to claim 1, characterized in that said at least one magnet is a permanent magnet.

3. The closing device according to claim 1, characterized in that said movement members comprise a linear module arranged parallel to said at least one cylindrical rod and comprising a tubular sheath and a transmission belt housed inside said tubular sheath and stretched between two return wheels driven by an electric gear motor; wherein a branch of said transmission belt associated with said slider is arranged outside the sheath and facing towards the magnetic plate integral with the sliding door.

4. The closing device according to claim 1, characterized in that said movement members comprise a linear module, arranged inside the at least one cylindrical rod, said linear module constituted by a transmission belt stretched between two return wheels driven by an electric gearmotor with a branch of said transmission having associated therewith said slider arranged inside said at least one cylindrical rod and turned towards said magnetic plate made integral with said sliding door.

5. The closing device according to claim 1, characterized in that said magnetic plate comprises at least one permanent magnet, configured to interact with said slider to drag said sliding door coupled thereto by a magnetic field produced by said cursor.

6. The closing device according to claim 1, characterized in that between said slider and said magnetic plate there is an inter-space so as to ensure sliding of the sliding door without friction.

7. The closing device according to claim 1, characterized in that coupling members are provided interposed between the sliding door and said at least one cylindrical rod, said coupling members comprising low friction coefficient bearings for carrying out a fluid translation of the sliding door, said coupling members provided with annular sealing members for sealing a coupling between the sliding door and the at least one cylindrical rod.

8. The closing device according to claim 1, characterized in that an internal face of said door, facing the access mouth is pressurizable in correspondence with the operative position, by at least one inflatable seal arranged in a closed ring in said frame to circumscribe the access mouth.

9. The closing device according to claim 1, characterized in that a sliding movement of said door dragged by said slider is horizontal, in that said at least one cylindrical rod is arranged horizontally in an upper part of the frame of said controlled contamination device and by low friction linear guide members provided to keep a lower part of the said sliding door close to said frame.

10. The closing device according to claim 1, characterized in that a sliding movement of said door dragged by said slider is vertical, and in that two cylindrical rods of said at least one cylindrical rod are provided, said two cylindrical rods having vertical orientation and symmetrically arranged with respect to said access mouth.

11. The closing device according to claim 1, characterized in that position sensors are provided for detecting and signalling movement into said operative and inoperative positions of the said sliding door.

* * * * *